July 1, 1975 C. DE GROOT Plant Pat. 3,736
BOXWOOD PLANT
Filed June 15, 1973
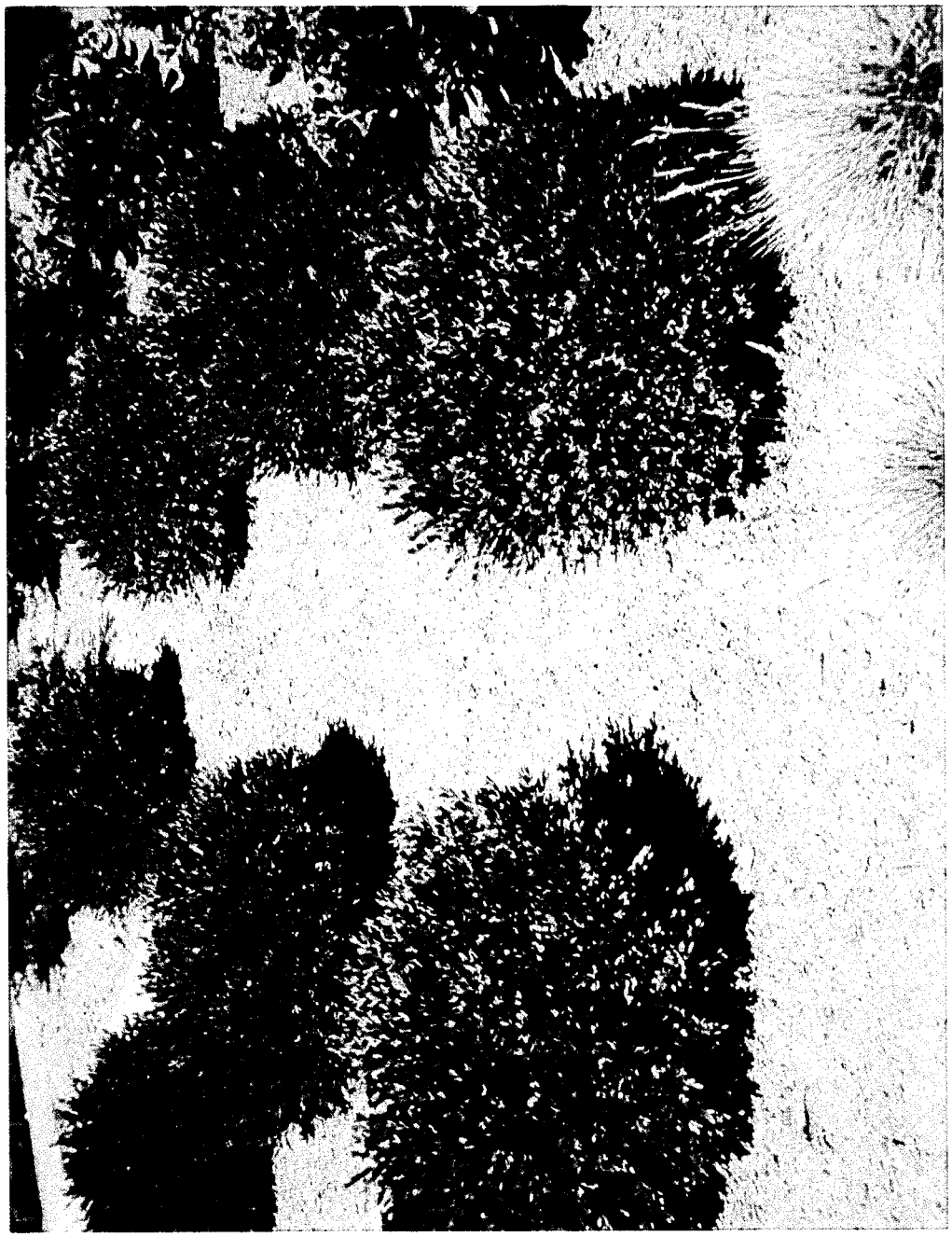

United States Patent

Plant Pat. 3,736
Patented July 1, 1975

3,736
BOXWOOD PLANT

Constant De Groot, Oakville, Ontario, Canada, assignor to Sheridan Nurseries Ltd., Toronto, Ontario, Canada Filed June 15, 1973, Ser. No. 370,435
Int. Cl. A01h 5/00
U.S. Cl. Plt.—54 1 Claim

ABSTRACT OF THE DISCLOSURE

This invention relates to a new and distinct variety of boxwood plant, and particularly to a Buxus hybrid.

In general, boxwood is a low growing, woody, broadleaf evergreen plant and has good growing properties both in sun and in shade. It can survive winter where the winter season is generally mild—as in southern Ontario, the Maritime provinces of Canada, and the northeast United States—and where a dependable snow cover throughout the winter may be assured. However, ordinary boxwood varieties, particularly Korean boxwood, may turn brown about November and remain brown until past March of the following spring, or the plants may produce large quantities of flowers or fruit. In addition, English boxwood is not as hardy, and may exhibit higher rates of winter kill. These characteristics are generally undesirable.

The present variety exhibits a uniform medium to dark olive green colour throughout the year, including winter, and produces substantially no flowers or fruit. In addition, the present variety has a shorter growth cycle when compared with common Korean boxwood, thus providing a plant having commercial worth since it may be marketed sooner than common Korean boxwood. The growth habit of the present Buxus hybrid is to a uniform globe shape thus obviating the need for constant trimming at the nursery.

With particular reference to the variety *Buxus microphylla koreana* "Wintergreen," the present variety has a number of characteristics which differ from those of the "Wintergreen" variety. For example, the present variety presents a dense, compact and globular shrub whereas "Wintergreen" is a loose, somewhat open and upright shrub. The internodes of the present variety are shorter than those of "Wintergreen," being typically in the order of 8–12 mm., whereas those of Wintergreen are 10–18 mm. The foliage of the present variety is a deeper green than that of "Wintergreen," and each leaf has a thinner, more supple texture than the thick, leathery texture of the leaves of "Wintergreen." The leaf size of the present variety is generally longer than that of "Wintergreen," and about the same width (typically, 16–20 mm. long and 6–9 mm. wide for the present variety; 12–15 mm. long and 6–9 mm. wide for "Wintergreen"). The yearly growth rate of the present variety is generally 4 to 6 cm., whereas that of "Wintergreen" is 4 to 13 cm.; resulting in the present variety being more dense, compact and dwarf than the variety "Wintergreen."

The present variety of boxwood plant is a hybrid coming as a cross between an English boxwood and a Korean boxwood; thereby inheriting the deeper green colour of the English boxwood and the hardiness of the Korean boxwood. Specifically the present variety arises as a hybrid coming from the cross:

*Buxus sempervirens "Suffruticosa"* × *Buxus microphylla koreana*

This new variety was first evaluated in 1959—the cross having been made in 1953, with the seedlings first germinated in 1954. Since 1959, cuttings have been taken at the nursery of Sheridan Nurseries Ltd., at 1116 Winston Churchill Boulevard, Oakville, Ontario; and this asexual reproduction has produced descendants which have exhibited the distinguishing characteristics of this new variety, thereby establishing that the strain is true.

More detailed description of the present variety follows, taken together with the drawing, in colour.

The drawing is a colour photograph, showing as well as possible by this method of illustration, the shape and natural colour of specimen plants of the new and distinct variety of Buxus hybrid according to this invention.

THE PLANT

TYPE: Broadleaf evergreen.
BREEDING: Hybrid.
PARENTAGE: *Buxus sempervirens "Suffruticosa"* × *Buxus microphylla koreana*
GROWTH HABIT: Low growing, dense, compact, uniform globe shaped, shorter growth cycle to marketable plant than common Korean boxwood; good winter hardiness. Yearly growth rate is about 4 to 6 cm. per year. New spring growth may have a faint bronze tinge.
FOLIAGE: Numerous, broad-leaf, 6 to 9 mm. wide by 16 to 20 mm. long (average, mature) ovoid shaped, medium thickness, smooth edge with short petiole. The internodes are about 8 to 12 mm. long.
COLOUR: Medium to dark olive green, without any general tendency to turn to brown through the winter months. Typical colour, according to the *Nickerson Colour Fan* published by Munsell Color Company, Incorporated of Baltimore, Md., is olive green 2.5YG4/3.
FLOWERS: Substantially none.
FRUIT: Substantially none; any fruit is hidden beneath the foliage.

The above description is of plants, asexually reproduced at Oakville, Ontario; and is of the Buxus hybrid as observed thereat.

I claim:

1. A new and distinct variety of Buxus hybrid plant, characterized by its shorter growth cycle, uniform globe shape, dense and compact growth habit, and deep olive green colour; and by its lack of any general tendency to turn brown-coloured through the winter months, and that it produces substantially no flowers or fruit.

References Cited

Monrovia Nursery Co. Wholesale Catalog for 1971, Azusa, Calif., p. 36 relied on.

ROBERT E. BAGWILL, Primary Examiner